US011450121B2

(12) United States Patent
Di Carlo et al.

(10) Patent No.: US 11,450,121 B2
(45) Date of Patent: Sep. 20, 2022

(54) LABEL-FREE DIGITAL BRIGHTFIELD ANALYSIS OF NUCLEIC ACID AMPLIFICATION

(71) Applicant: The Regents of the University of California, Oakland, CA (US)

(72) Inventors: Dino Di Carlo, Los Angeles, CA (US); Aydogan Ozcan, Los Angeles, CA (US); Omai B. Garner, Culver City, CA (US); Hector E. Munoz, Los Angeles, CA (US); Carson Riche, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1122 days.

(21) Appl. No.: 16/019,421

(22) Filed: Jun. 26, 2018

(65) Prior Publication Data
US 2018/0373921 A1     Dec. 27, 2018

Related U.S. Application Data

(60) Provisional application No. 62/525,699, filed on Jun. 27, 2017.

(51) Int. Cl.
G06V 20/69         (2022.01)
G06T 7/00          (2017.01)
(Continued)

(52) U.S. Cl.
CPC .......... *G06V 20/695* (2022.01); *G06T 7/0012* (2013.01); *G06V 10/464* (2022.01);
(Continued)

(58) Field of Classification Search
CPC .. G06V 20/695; G06V 10/464; G06V 20/698; G06T 7/0012; G06T 2207/30072;
(Continued)

(56) References Cited

U.S. PATENT DOCUMENTS 6,174,670 B1   1/2001 Wittwer et al.
7,374,879 B2   5/2008 Mori et al.
(Continued)

FOREIGN PATENT DOCUMENTS

AU   2015249846 A2 * 11/2016  ............. C12N 15/10
CA   2505151 C  *  7/2013  ........... C12Q 1/6837
(Continued)

OTHER PUBLICATIONS

Csurka, Gabriella et al., Visual Categorization with Bags of Keypoints, Xerox Research Centre Europe, 6, chemin de Maupertuis, 38240 Meylan, France, https://www.researchgate.net/publication/228602850 (17pages).
(Continued)

Primary Examiner — Steven P Sax
(74) Attorney, Agent, or Firm — Vista IP Law Group LLP

(57) ABSTRACT

An optical readout method for detecting a precipitate (e.g., a precipitate generated from the LAMP reaction) contained within a droplet includes generating a plurality of droplets, at least some which have a precipitate contained therein. The droplets are imaged using a brightfield imaging device. The image is subject to image processing using image processing software executed on a computing device. Image processing isolates individual droplets in the image and performs feature detection within the isolated droplets. Keypoints and information related thereto are extracted from the detected features within the isolated droplets. The keypoints are subject to a clustering operation to generate a plurality of visual "words." The word frequency obtained for each droplet is input into a trained machine learning droplet classifier, wherein the trained machine learning droplet classifier classifies each droplet as positive for the precipitate or negative for the precipitate.

19 Claims, 11 Drawing Sheets

(51) Int. Cl.
*G16B 40/10* (2019.01)
*G06V 10/46* (2022.01)
*C12Q 1/6844* (2018.01)

(52) U.S. Cl.
CPC ........... *G06V 20/698* (2022.01); *G16B 40/10* (2019.02); *C12Q 1/6844* (2013.01); *G06T 2207/30072* (2013.01)

(58) Field of Classification Search
CPC ............... G16B 40/10; C12Q 1/6844; C12Q 2531/119; C12Q 2563/159; C12Q 2565/601; G06N 20/00
See application file for complete search history.

(56) References Cited

U.S. PATENT DOCUMENTS

| | | | | |
|---|---|---|---|---|
| 9,177,225 | B1 * | 11/2015 | Cordova-Diba | G06V 20/20 |
| 9,240,043 | B2 * | 1/2016 | Christiansen | G06V 20/698 |
| 9,348,920 | B1 * | 5/2016 | Kesin | G06F 16/93 |
| 9,390,086 | B2 * | 7/2016 | Lisuk | G06F 40/117 |
| 9,708,657 | B2 * | 7/2017 | Asbury | G16H 50/30 |
| 10,093,967 | B2 * | 10/2018 | Walter | C12Q 1/6816 |
| 2009/0325810 | A1 * | 12/2009 | Lapointe | G16B 25/00 |
| | | | | 506/7 |
| 2010/0223276 | A1 * | 9/2010 | Al-Shameri | G06F 16/2264 |
| | | | | 707/769 |
| 2012/0157160 | A1 | 6/2012 | Ozcan et al. | |
| 2013/0054603 | A1 * | 2/2013 | Birdwell | G06K 9/6224 |
| | | | | 707/738 |
| 2014/0247973 | A1 * | 9/2014 | Moussavi | G06K 9/6277 |
| | | | | 382/133 |
| 2016/0006730 | A1 * | 1/2016 | Chari | G06F 21/32 |
| | | | | 726/7 |
| 2016/0257990 | A1 | 9/2016 | Di Carlo et al. | |
| 2017/0260585 | A1 * | 9/2017 | Lapointe | G16B 40/20 |
| 2017/0342408 | A1 * | 11/2017 | Jayaprakash | C07K 16/00 |
| 2018/0034784 | A1 * | 2/2018 | Sinclair | H04L 63/0428 |

FOREIGN PATENT DOCUMENTS

| | | | | |
|---|---|---|---|---|
| CA | 2908527 | A1 * | 10/2014 | ............. C07K 16/18 |
| CN | 108027849 | B * | 3/2020 | ............ B01L 3/0275 |
| CN | 107735497 | B * | 8/2021 | ........... C12Q 1/6827 |
| CN | 107750277 | B * | 11/2021 | ........... C12Q 1/6809 |
| WO | WO-2005071058 | A2 * | 8/2005 | ........... C07K 14/705 |
| WO | WO-2015168026 | A2 * | 11/2015 | ......... G01N 15/1475 |
| WO | WO-2016075096 | A1 * | 5/2016 | ............ G06K 9/0014 |
| WO | WO-2017046799 | A1 * | 3/2017 | ......... G01N 21/8851 |
| WO | WO-2017218202 | A1 * | 12/2017 | ................ C12Q 1/18 |

OTHER PUBLICATIONS

Kong, Janay E. et al., Highly Stable and Sensitive Nucleic Acid Amplification and Cell-Phone-Based Readout, ACS Nano 2017, 11, 2934-2943.

Navruz, Isa et al., Smart-phone based computational microscopy using multi-frame contact imaging on a fiber-optic array, Lab Chip, Oct. 21, 2013; 13(20): 4015-4023.

Riche, Carson T. et al., Flow invariant droplet formation for stable parallel microreactors, Nature Communications, 7:10780, DOI: 10.1038/ncomms10780, www.nature.com/naturecommunications (7pages).

Van der Maaten, Laurens et al., Accelerating t-SNE using Tree-Based Algorithms, Journal of Machine Learning Research 15 (2014) 3221-3245.

* cited by examiner

Strong Positive Words

Weak Positive Words

Strong Negative Words

Weak Negative Words

LABEL-FREE DIGITAL BRIGHTFIELD ANALYSIS OF NUCLEIC ACID AMPLIFICATION

RELATED APPLICATION

This Application claims priority to U.S. Provisional Patent Application No. 62/525,699 filed on Jun. 27, 2017, which is hereby incorporated by reference in its entirety. Priority is claimed pursuant to 35 U.S.C. § 119 and any other applicable statute.

STATEMENT REGARDING FEDERALLY SPONSORED RESEARCH AND DEVELOPMENT

This invention was made with Government support under 1332275, awarded by the National Science Foundation. The Government has certain rights in the invention.

TECHNICAL FIELD

The technical field generally relates to methods for the detection of nucleic acid. More specifically, the technical field relates to methods for detecting nucleic acid such as DNA in small confined volumes (e.g., droplets) using Loop-mediated Isothermal Amplification (LAMP) although the method may find applicability with other amplification techniques.

BACKGROUND

Single-molecule or single-cell assays (e.g., digital PCR, digital loop-mediated isothermal amplification (LAMP), digital ELISA, drop-Seq) require fractionating or compartmentalizing a large volume to such a level that each smaller fractionated volume contains either none (0) or a single (1) entity of interest (i.e., a digital assay). Digital LAMP allows for improved quantification accuracy by counting single droplets with amplified DNA. The initial concentration of that target nucleic acid (e.g., DNA) is directly correlated to the number of droplets with amplified nucleic acid. One approach to detect and measure the amplification of DNA via LAMP relies on the presence or absence of a by-product, magnesium pyrophosphate, which precipitates out during the LAMP amplification process. This enables the user to assess the turbidity of the volume as a proxy for DNA production. See e.g., U.S. Pat. No. 7,374,879. This turbidity is observed in 100 microliter to 1 milliliter scale volumes because the volume is well mixed and the light scattered from many precipitate particles can be observed. However, in smaller e.g. nanoliter-scale volumes in microwells precipitate was not observed. This may be because precipitate growth is seeded at interfaces of the solid chamber surrounding the fluid and is not observable using brightfield imaging or light scattering, or because the small volume small precipitate particles do not have sufficient interactions before they settle to the microwell surface to coalesce to a larger size precipitate particle that is observable by microscopic imaging. Alternative technologies rely on pH sensitive indicators or metal-sensitive colorimetric indicators based on calcein, hydroxynaphthol blue, EvaGreen®, or malachite green. Currently, a main approach to perform compartmentalization of a sample volume in a uniform manner relies on creating monodisperse emulsions of drops or droplets using microfluidic approaches that create aqueous droplets in am immiscible (e.g., oil) phase. For readout purposes, standard technology uses fluorescent DNA intercalating dyes to detect DNA. Unfortunately, to readout whether a particular droplet is positive or negative requires the use of fluorescent dyes. Not only do fluorescent dyes increase the cost of the overall assay, the fluorescent dye itself can interfere with the reaction kinetics. Moreover, fluorescent based readout systems require complex and costly optical systems. For example, fluorescent microscopes require one or more excitation light sources in addition to expensive optics including specialized filters. A new method of digital LAMP (or other amplification/reaction methods that generate a precipitate) is needed that does not rely on the use of fluorescent dyes such that the droplets may be interrogated without the need of a fluorescent microscope device.

SUMMARY

In one embodiment, an optical readout method for detecting a precipitate (e.g., a precipitate generated from a LAMP reaction such as magnesium pyrophosphate) contained within a droplet includes generating a plurality of droplets, at least some which have the precipitate contained therein. Because of the rounded shape of the droplet and the free surface of the droplet which precipitate does not adhere to, precipitate from the entire droplet volume can accumulate under gravity to the bottom center of the droplet (i.e., the lowest point of the droplet interior). Because of the geometry and free surface of the liquid drop, sufficient precipitate particles can accumulate to become easily visible using microscopic imaging. The droplets are imaged using a brightfield imaging device. The image is subject to image processing using image processing software executed on a computing device. The computing device may include a laptop, desktop, or remote server, or the like.

Image processing isolates individual droplets in the image from the brightfield imaging device and performs feature detection within the isolated droplets. Keypoints and information related thereto are extracted from the detected features within the isolated droplets. The keypoints are subject to a clustering operation to generate a plurality of visual "words" that are associated with a particular droplet. The word frequency obtained for each droplet is input into a trained machine learning droplet classifier, wherein the trained machine learning droplet classifier classifies each droplet as positive for the precipitate or negative for the precipitate.

In some embodiments, additional image features are used in combination with word frequency to classify droplets as positive or negative. For example, the additional image features may include one or more strongly negative words (words that are associated with a negative droplet) that may appear. Likewise, the additional feature may include one or more strongly positive words (words that are associated with a positive droplet). The additional image features may include words that are located in the center region of the droplet (likely precipitate contained in droplet) and words that are located outside the center of the droplet (likely no precipitate contained in the droplet). In another option, the additional image features may include statistical information of the Laplacian of Gaussian Transformation of the image.

In one embodiment, the droplets are generated using a microfluidic device and contain a loop-mediated isothermal amplification (LAMP) reaction mix, DNA primers specific to a target nucleic acid, and the target nucleic acid sample. The droplets are incubated for a period of time and then imaged using a brightfield imaging device to obtain one or more images of the droplets. The droplets are processed using image processing software as described above.

In another embodiment, a method for detecting a nucleic acid amplification reaction that generates a precipitate within a droplet includes the operations of generating a plurality of droplets containing an analyte solution comprising target nucleic acid molecules, nucleic acid amplification reaction mix, and primers. The nucleic acid amplification reaction mix is then reacted for a time period to generate products within the plurality of droplets containing a target nucleic acid molecule, wherein the products comprise a precipitate. The precipitate accumulates within a central region of the droplet at its lowest point (due to gravity). The plurality of droplets are then imaged using an imaging device to obtain one or more images. The one or more images are then subject to image processing using image processing software executed on a computing device. The image processing includes isolating individual droplets contained in the one or more images. Automatic feature detection of features associated with the presence of precipitate within the isolated droplets in the one or more images is then performed. The plurality of droplets are then classified by the image processing software as positive or negative for nucleic acid target molecules based on the presence of the detected features in a center region of the droplets.

In another embodiment, a system for the optical readout of droplets containing a precipitate therein includes a microfluidic device configured to generate a plurality of droplets, some of the plurality of droplets comprising a precipitate contained therein. A brightfield imaging device is provided that is configured to obtain an image of a field of view (FOV) containing the plurality of droplets. The system further includes a computing device configured to execute image processing software. The image processing software is configured to: isolate individual droplets in the image; perform feature detection within the individual droplets in the image; extract keypoints and information related thereto from the detected features within the individual droplet; clustering the keypoints to generate a plurality of words; input the word frequency into a trained machine learning droplet classifier executed by the image processing software, wherein the trained machine learning droplet classifier classifies each droplet as positive for the precipitate or negative for the precipitate. Additional image features may also be input into the trained machine learning droplet classifier as described above.

While the droplets may be generated using a microfluidic device that generates droplets it should be appreciated that different methods of droplet generation may be used to form the droplets. For example agitation or shaking may be used to generate the droplets. Typically, the droplets are formed from an aqueous solution that is contained in an oil-based carrier. Of course, the methods may also work in other instances where the droplet is oil-based and the carrier is aqueous-based.

The methods and system disclosed herein can read out amplified DNA via LAMP in droplets and potentially other nucleic acid amplification tests. The output is achieved with brightfield microscopy, which is an improvement to the more complicated and costly fluorescent readout currently used. No intercalator dye or sequence specific probes are needed in this assay. In addition, precipitates are likely to be more thermal and light stable than fluorescent dyes, allowing the reaction to be performed without concern for limiting light exposure, or allowing storage over a longer period of time.

DETAILED DESCRIPTION OF THE ILLUSTRATED EMBODIMENTS

Figure 1:
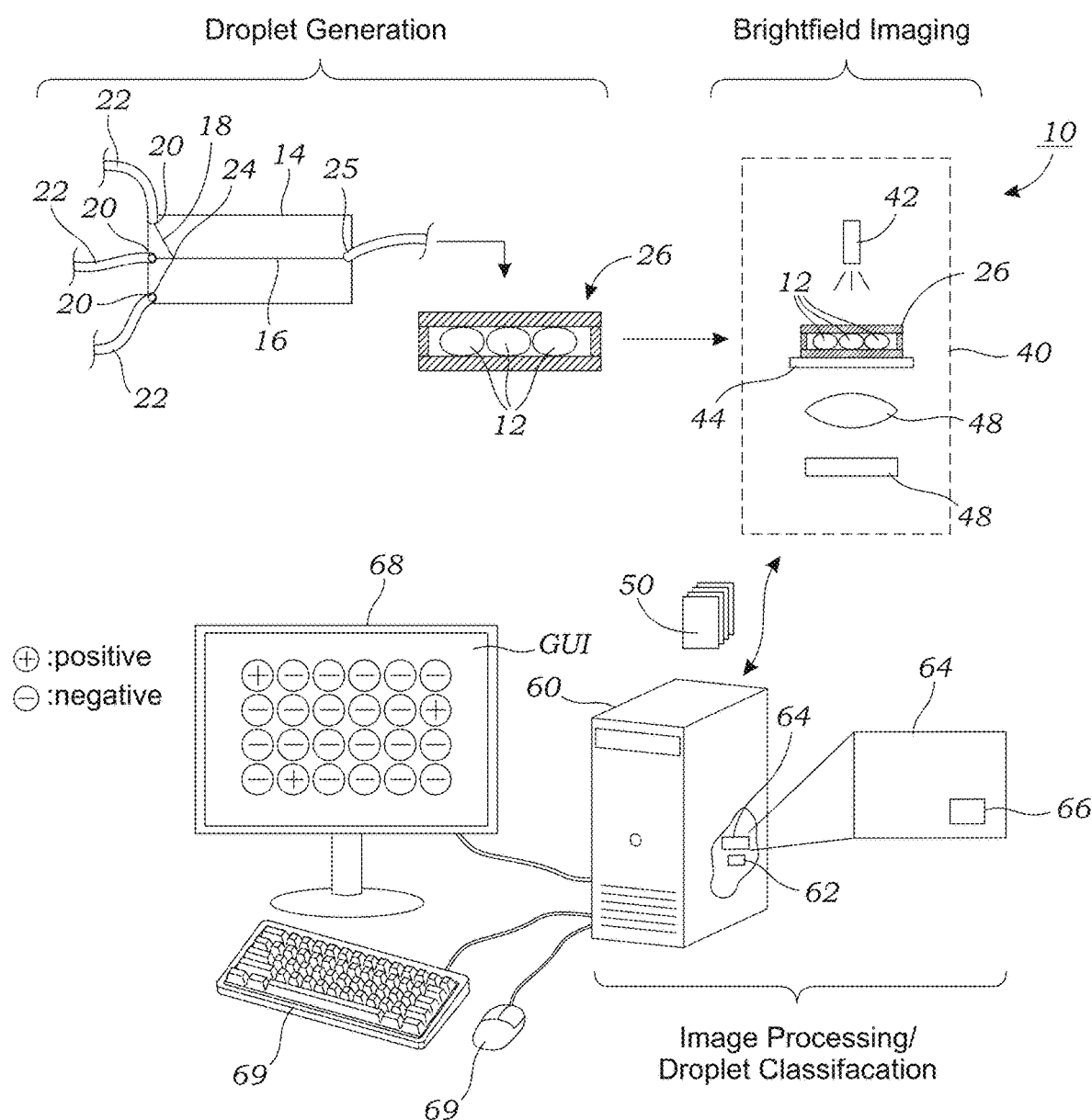
FIG. 1 illustrates one embodiment of a system for the optical readout of droplets containing a precipitate therein.

FIG. 1 illustrates an embodiment of a system 10 for the optical readout of droplets 12. The droplets 12 that are optically read by the system 10 either contain a precipitate or are free of the precipitate. Droplets 12 that contain the precipitate are classified as positive (+) while those droplets 12 that do not contain the precipitate are classified as negative (−). In one particular embodiment as explained herein, the precipitate is a pyrophosphate (e.g., magnesium pyrophosphate) that is generated as a result of a chemical reaction that takes place inside the droplet 12. For example, in one preferred embodiment, the precipitate is generated in the droplet 12 by a loop-mediated isothermal amplification (LAMP) reaction that takes place inside droplets 12 that contain a target nucleic acid sequence. The target nucleic acid may be an oligonucleotide or DNA segment with a specific sequence that is targeted by the LAMP reaction. When present in the initial sample that is used to generate the droplets 12 as explained below, this creates some droplets 12 that contain the target nucleic acid while other droplets do not contain the target nucleic acid. In those droplets 12 that contain the target nucleic acid, the LAMP process amplifies the target nucleic acid which also forms a precipitate within the droplet 12. Because the droplet 12 has a spherical shape, precipitate that is denser than the solution settles under gravity and accumulates in the bottom center of the spherical droplet 12 (i.e., the lowermost region of the interior of the droplet 12). This settling increases the effective size of precipitate or cluster of precipitates and leads to the ability to identify the presence of precipitate, which is not possible with flat bottom microwells for example which hold similar fluid volumes. Preferably, the droplets 12 are kept stationary without substantial fluid or droplet motion or mixing for a period of time (10 min to 2 hours), either during the amplification reaction or following reaction to enable the settling and accumulation of precipitate. The presence of this precipitate is then used to classify the droplet 12 as positive (+). The system 10 may use the percentage or ratio of positive droplets 12 to negative droplets 12 (or vice versa) to determine the initial concentration of target nucleic acid in the original sample.

Still referring to FIG. 1, in one embodiment, the droplets 12 are generated using a microfluidic device 14. The microfluidic device 14 contains a central microfluidic channel 16 along with two (or more) branch channels 18 with each respective channel having its own respective inlet 20. The inlets 20 are coupled to tubing 22 or the like that connect to a pumping source (not shown) which may include syringe pumps or any other type of pump used in connection with microfluidic devices. The two branch channels 18 intersect with the central microfluidic channel 16 to form a junction 24 where droplets 12 are formed. In a typical setup, an aqueous solution that contains the target nucleic acid (if present) as well as the LAMP reaction mix and DNA primers specific to a target nucleic acid is pumped or otherwise delivered to the microfluidic device 14 via the central microfluidic channel 16. Details regarding the LAMP reaction, reaction mix, and use of primers may be found in Kong et al., D. Highly Stable and Sensitive Nucleic Acid Amplification and Cell-Phone-Based Readout. ACS Nano 2017, 11 (3), 2934-2943, which is incorporated herein by reference.

An oil-based carrier solution (e.g., an immiscible fluorocarbon oil such as Fluorinert™ FC-40) is pumped or otherwise flowed into the microfluidic device 14 via the two branch channels 18. An optional surfactant (e.g., fluorosurfactant available from RAN Biotechnologies) may also be used to stabilize the oil-water interface for the droplets 12. In this configuration, droplets 12 are generated at the junction 24. Preferably, the droplets 12 that are generated are substantially monodisperse in size (e.g., diameter). Typically, the diameter of the droplets 12 is in the size range of about 50 µm to about 150 µm. In the experiments described herein, studies were performed by adding serially diluted λ DNA (available from Thermo Fisher) to form droplets 12. The LAMP solution was prepared and co-injected into the microfluidic device 14 with the Fluorinert™ FC-40 and RAN fluorosurfactant.

As seen in FIG. 1, the formed droplets 12 are removed from the microfluidic device 14 via outlet 25 and placed within a chamber 26. The chamber 26 is formed from an optically transparent material (to allow for imaging) and defines a three-dimensional volume that holds a plurality of droplets 12 in a two-dimensional array. The height of the chamber 26 is advantageously made so that only a single layer of droplets 12 is formed (e.g., 50 µm). Further, the height of the chamber 26 is such that the droplets 12 contact both the upper and lower surfaces and are somewhat squeezed to form oblong-shaped droplets 12 (e.g., the height is less than the diameter of the droplets 12). This ensures that the precipitate, if formed, forms in a uniform location and also aids in removing artifacts in the images that are obtained. For the LAMP reaction, the droplets 12 are incubated at an elevated temperature (e.g., 67° C.) for a period of time (e.g., two hours). Incubation may take place prior to transfer of the droplets 12 to the chamber 26 or within the chamber 26. In other embodiments, incubation may also take place in the microfluidic device 14. In the experiments conducted herein, droplets 12 were transferred from the microfluidic device 14 to a 0.5 mL microcentrifuge tube for incubation prior to transfer to the chamber.

After the droplets 12 have been loaded or transferred into the chamber 26, the chamber 26 is imaged using a brightfield imaging device 40. The brightfield imaging device 40 may include a conventional brightfield microscope in one embodiment. The brightfield imaging device 40 includes an illumination source 42 for illuminating the droplets 12 contained within the chamber 26 which is mounted on a sample support 44. The brightfield imaging device 40 includes one or more magnification lenses 46 along with an image sensor 48 that captures images of the droplets 12 (experiments were conducted at 10× magnification). The images of the droplets 12 may be captured as image files 50 generated in any number of digital image formats such as TIFF, JPG, PNG, Zeiss *.LSM, Leica *.LEI and *.LIF, Volocity, SimplePCI *.CXD, and the like. In some embodiments, the brightfield imaging device 40 may need to scan the area of the chamber 26 to capture all of the droplets 12 that are contained therein. The scanning may be accomplished, for example, using a scanning sample support 44. In other embodiments, however, the field-of-view (FOV) may be sufficiently large to capture the droplets 12 without scanning.

In alternative embodiments, the brightfield imaging device 40 may include a portable microscope device that is used in conjunction with portable electronic devices such as mobile phones (e.g., Smartphones) or other devices such as tablet computers. For example, field-portable transmission microscopes that use a mobile phone to image a sample over a wide field-of-view (FOV) are known. See Navruz et al., Smart-phone based computational microscopy using multi-frame contact imaging on a fiber-optic array, Lab Chip, 13(20), pp. 4015-23 (2013) and U.S. Published Patent Application No. 2012-0157160 (Compact Wide-Field Fluorescent Imaging on a Mobile Device), which are incorporated herein by reference. The brightfield imaging device 40 may include a field-portable device that is able to image a wide FOV of a sample using the camera functionality of the underlying portable electronic device.

FIG. 1 also illustrates a computing device 60 that is used to acquire and process the image files 50. The computing device 60 may include a personal computer, laptop, server, or the like. The computing device 60 may be co-located with the brightfield imaging device 40 or it may be located remotely from the brightfield imaging device 40. For example image files 50 may be transmitted over a local area network or wide area network (e.g., Internet) to a remotely located server or the like for image acquisition and processing. Image files 50 may also be transferred via a wired connection between the brightfield imaging device 40 and computing device 60 or using a wireless connection. The computing device 60 contains one or more processors 62 therein that are used to execute image processing software 64. The image processing software 64 as described herein performs several functions including: isolating individual droplets 12 in the images; performing feature detection within the individual droplets 12 in the images (to find potential precipitate); extracting keypoints and information related thereto from the detected features within the individual droplet 12; clustering the keypoints to generate a plurality of visual "words" in a bag-of-words; input the visual "word" frequency into a trained machine learning droplet classifier 66 also executed by the image processing software 64, wherein the trained machine learning droplet classifier 66 classifies each droplet 12 as positive (+) for the precipitate or negative (−) for the precipitate.

Figure 10:
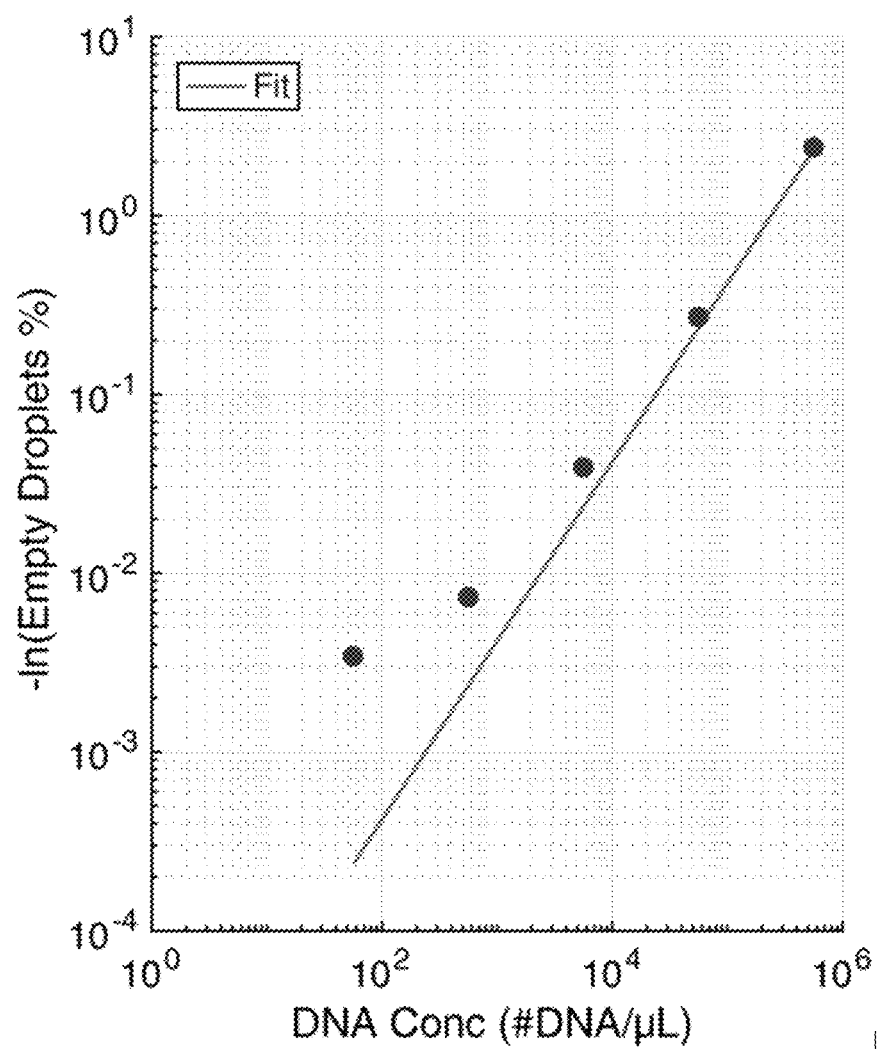
FIG. 10 illustrates a curve illustrating DNA copy number as a function of empty droplet percentage (natural log).

The image processing software 64 is also configured to count the total number of positive (+) droplets 12 and the total number of negative (−) droplets 12. In some embodiments, the image processing software 64 is also configured to calculate the size and/or volume of the droplets 12. The image processing software 64 also is configured to calculate a ratio or percentage of positive (+) droplets 12 in the total number of droplets 12 (the ratio could be also be compared to negative (−) droplets 12 or negative (−) to positive (+) droplets 12. In one embodiment, this ratio or percentage is further used to calculate an initial concentration of target nucleic acid. For example, counting the ratio or percentage of positive (+) droplets 12 (or negative (−) droplets 12) may be used to determine the concentration of the target nucleic acid using the Poisson distribution of molecules or targets. In some embodiments the ratio of positive (+) droplets 12 (or negative (−) droplets 12) for a particular size range of droplets 12 or a combination of size ranges is used to determine the concentration by comparing with volume-dependent expectations based on Poisson statistics. FIG. 10 illustrates how the percentage of empty droplets is proportional to the original DNA concentration, although there are fewer empty droplets at low DNA count as expected. Appropriate curve fitting functions may be applied to deal with non-linearity at lower DNA copy numbers.

Results may also include a qualitative result or finding such as a "positive" or "negative" finding for a particular sample which may be used to detect the presence or absence of target nucleic acid in the sample. This may be based on a threshold number of positive (+) droplets 12 or a percentage/ratio that meets or exceeds a pre-determined threshold value (e.g., more than 2% of droplets 12 identified as positive (+) enables one to qualitatively say that the sample was positive for the target nucleic acid).

FIG. 1 also illustrates a display 68 that is associated with or connected to the computing device 60. The display 68 can be used to display images of the droplets 12 contained in the image files 50. The display 68 may also be used to identify the classification of the droplets 12 (e.g., positive (+) or negative (−)). The display 68 may also be used to display quantitative and/or qualitative results obtained using the system 10. A graphical user interface (GUI) may be provided so that the user can adjust parameters and features using an input device 69 (e.g., keyboard, mouse, or the like) used in the image processing process as described herein.

Figure 2:
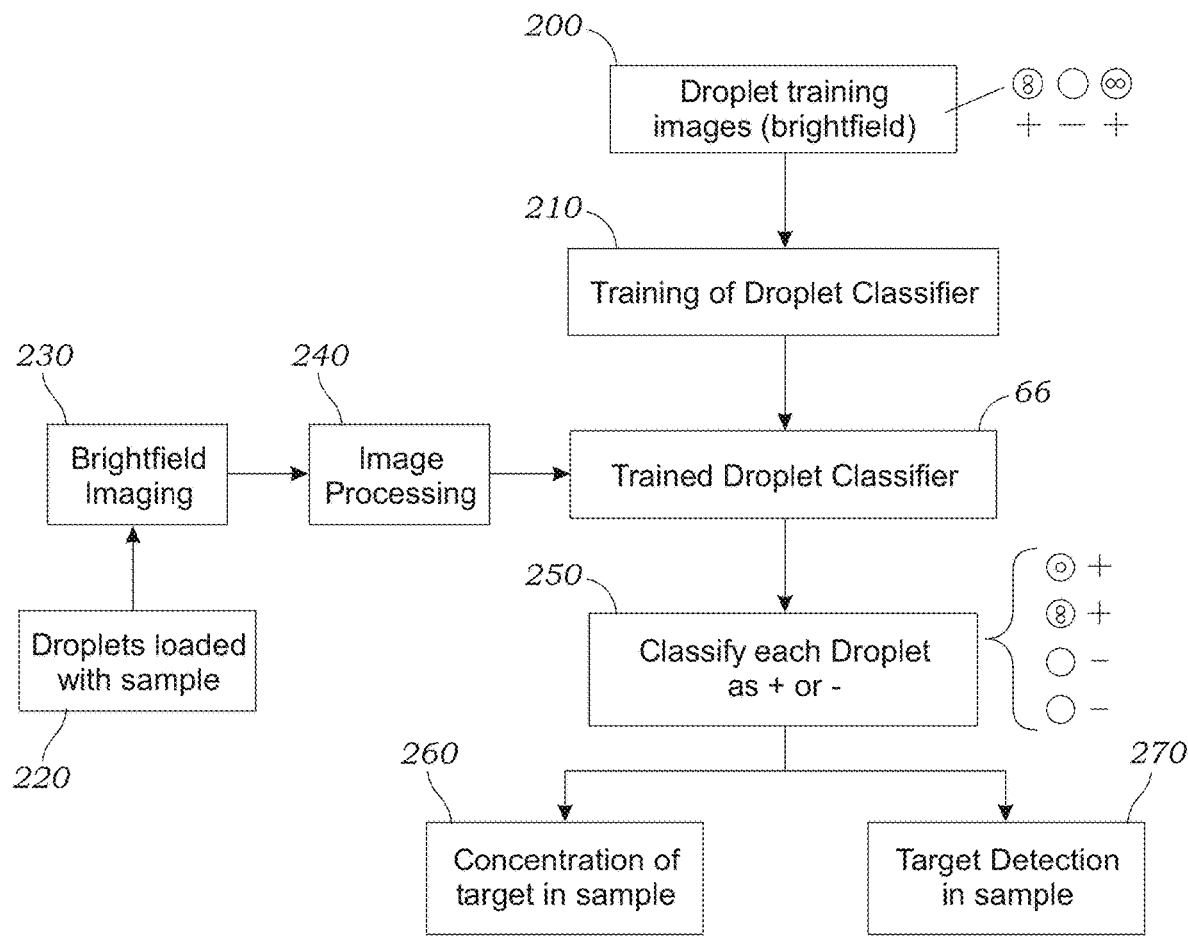
FIG. 2 illustrates a high-level overview of the optical readout method for target nucleic acid detection.

FIG. 2 illustrates a high-level overview of the optical readout method for target nucleic acid detection. As noted above, the method requires a trained machine learning droplet classifier 66 that is used to classify each droplet 12 as positive (+) or negative (−). Operation 200 of FIG. 2 illustrates that droplet training images of droplets 12 are obtained using brightfield imaging that are known to either be positive (+) or negative (−) along with training droplets 12. These "gold standard" training droplets 12 are then used to train the machine learning droplet classifier 66 as seen in operation 210. The training droplets 12 may be used with validation droplets 12 to confirm the proper training of the machine learning droplet classifier 66. Once the machine learning droplet classifier 66 has been trained, the trained machine learning droplet classifier 66 can be used to classify droplets 12. As seen in operation 220 of FIG. 2, droplets 12 are generated that are loaded with the sample (e.g., containing or thought to contain the target nucleic acid) as well as the amplification reaction mix/reagents. These droplets 12 are then optionally incubated and then subject to brightfield imaging as seen in operation 230. The image files 50 that are obtained in operation 230 are then subject to image processing 240 as described herein in more detail. This includes isolating the individual droplets 12, finding features and keypoints contained within the droplets 12, and clustering of these keypoints into visual words. After image processing 240, the word frequency and other image features are then input into the now trained machine learning droplet classifier 66. The trained machine learning droplet classifier 66 then classifies each droplet 12 as either positive (+) or negative (−) as seen in operation 250. As explained herein, the image processing software 64 may then use this information to output or generate a concentration of the target nucleic acid in the sample as seen in operation 260. The image processing software 64 may also (or in addition to), output a qualitative analysis of the sample as seen in operation 270. This may be, for example, outputting or generating a positive/negative indication for the presence in the sample of the target nucleic acid.

Figure 3:
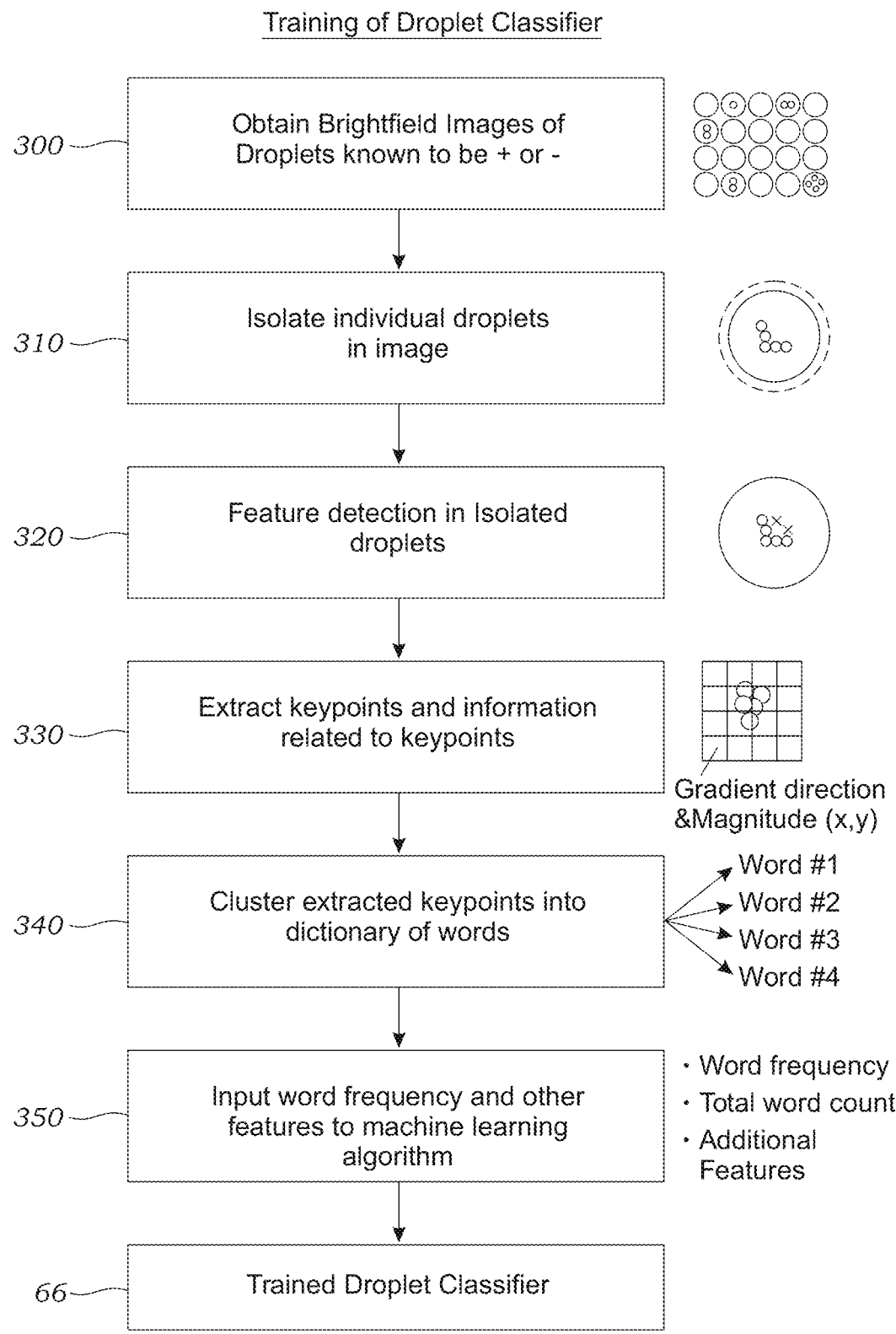
FIG. 3 illustrates a more detailed illustration of the workflow that is used to create the trained machine learning droplet classifier.
Figure 4:
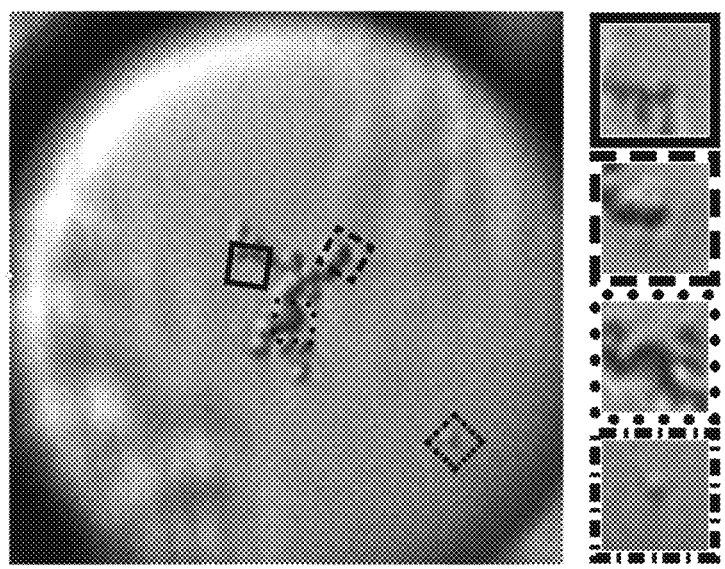
FIG. 4 illustrates an example of extracted SURF keypoints.
Figure 11:
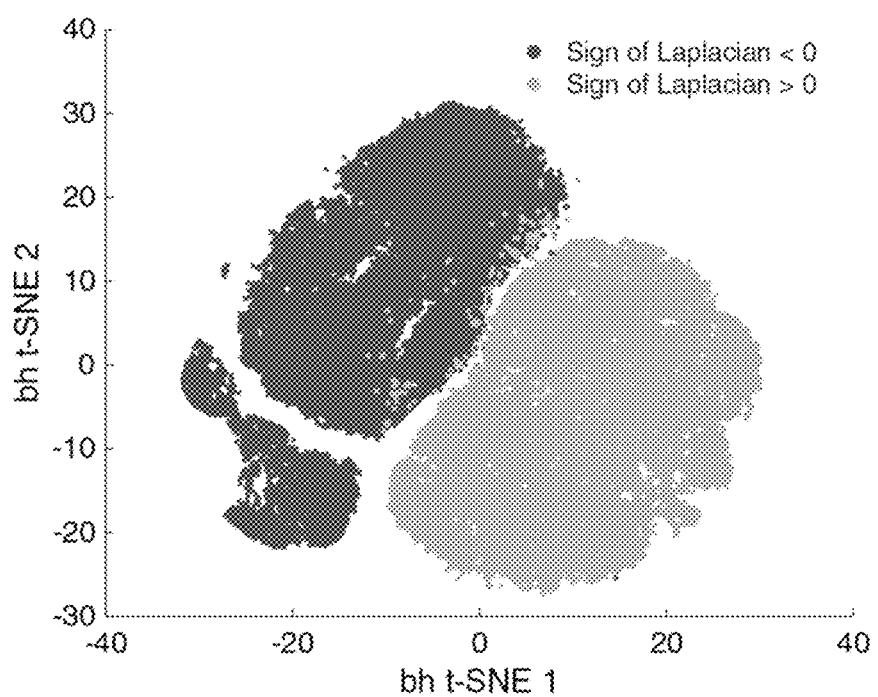
FIG. 11 illustrates a graphic representation of the SoL of SURF keypoints in two dimensions (instead of 64-dimensional descriptors) using the bh-tSNE algorithm.

FIG. 3 illustrates a more detailed illustration of the workflow that is used to create the trained machine learning droplet classifier 66 (e.g., operation 210 of FIG. 2). First, as seen in operation 300, brightfield images are obtained of droplets 12 that are known to be positive (+) or negative(−). The image files 50 are then subject to image analysis as seen in operation 310 to isolate individual droplets 12 in the image. For example, using the commercially available MATLAB program, the circular objects may be found using the circular Hough transform (CHT) function imfindcircles. CHT is a feature extraction technique used in digital image processing for detecting circular objects in a digital image. Next various image features are detected within the different droplets 12 in operation 320 and keypoints and information pertaining thereto are extracted as seen in operation 330. Keypoints have features similar to beads on a string or fractal grape-like structures, with punctate changes in intensity over the 1-5 micron scale, but not smooth gradients in intensity. In one embodiment, Speeded Up Robust Features (SURF) keypoints are extracted from each droplet in local regions of high contrast. FIG. 4 illustrates an example of extracted SURF keypoints. Each SURF keypoint is then described by dividing the region around the keypoint into sixteen (16) sub-regions, where four (4) horizontal and vertical wavelet responses are summed, resulting in a 64-dimensional feature space for each keypoint. Additionally, the sign of Laplacian (SoL), which indicates if the keypoint represents a white blob on a dark background (positive or +) or white blob on dark background (negative or −) is also calculated. FIG. 11 illustrates a graphic representation of the SoL of SURF keypoints using the bh-tSNE algorithm. Although the SoL of each SURF keypoint is not explicitly included in the descriptor-space, it is useful in describing the higher dimensional organization. Therefore, keypoints are first separated by SoL before clustering. While SURF is described as being used to generate keypoints other methods such as Scale Invariant Feature Transform (SIFT) may be used. In embodiments in which droplets 12 of different sizes are analyzed, separate training of the machine learning classifier 66 for each size droplet 12 is useful to take into account different precipitate amounts and structures that may be size dependent.

The number of keypoints in any one image varies, preventing the keypoints and their features from being used directly in classification methods. To address this, the method employs a Visual Bag of Words (VBoW) method that identifies the contents of an image by the frequency of image patches, or visual words (i.e., "words"). Images that contain the same class of objects will have similar frequencies of these visual words. The extracted SURF keypoints are clustered in 64-dimensional spaces to identify similar keypoints, and create a dictionary of words as seen in operation 340 of FIG. 3. The number of words in the dictionary may vary. Too few words will result in clustering dissimilar keypoints, while too many words will be too granular, and fail to describe images generally. As explained below, it was found that about eight words (not counting sub-categories) provided good performance. Of course, it should be understood that the method may be applied using different numbers of words.

Figure 5:
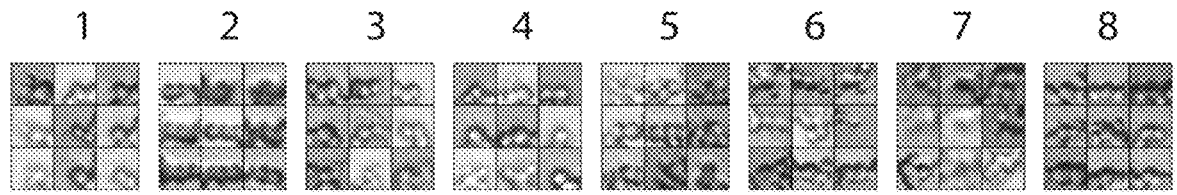
FIG. 5 illustrates exemplary images of different visual word clusters. SURF keypoints are divided into four sub-categories according to SURF metrics and sign of Laplacian prior to clustering: Strong Positive, Weak Positive, Strong Negative, and Weak Negative. Strong and Weak words occupy the same SURF keypoint descriptor space and are separated by SURF metric cutoff. Example images are closest to the center of the center of each visual word's descriptor space.
Figure 5:
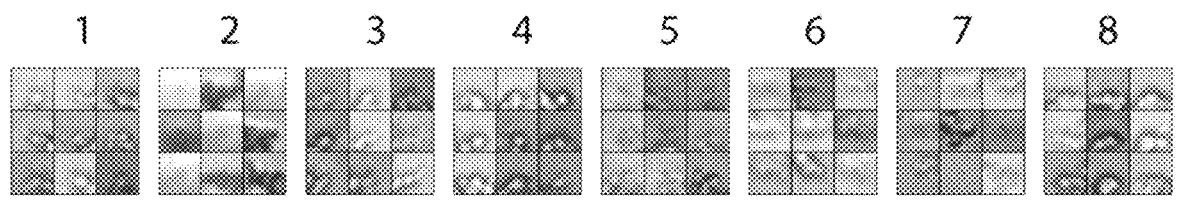
Figure 5:
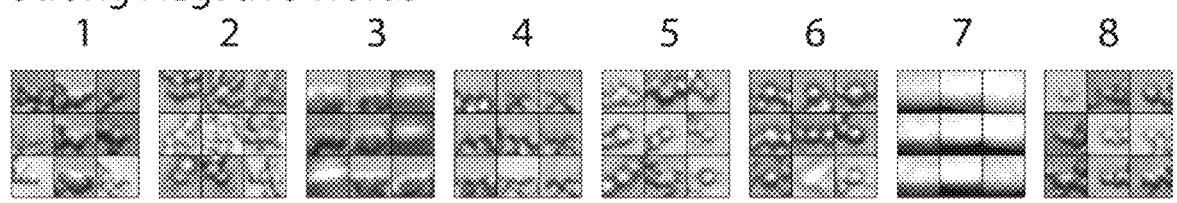
Figure 5:
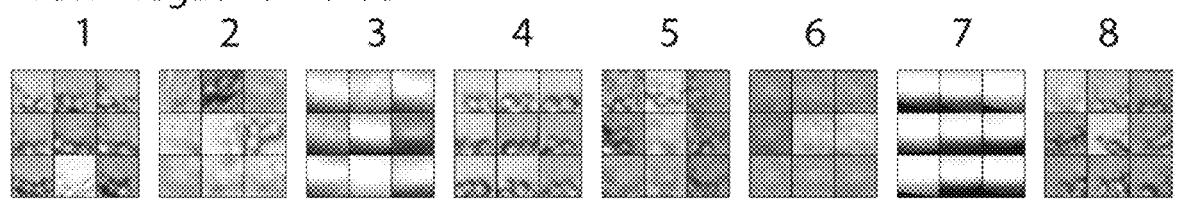
Figure 12A:
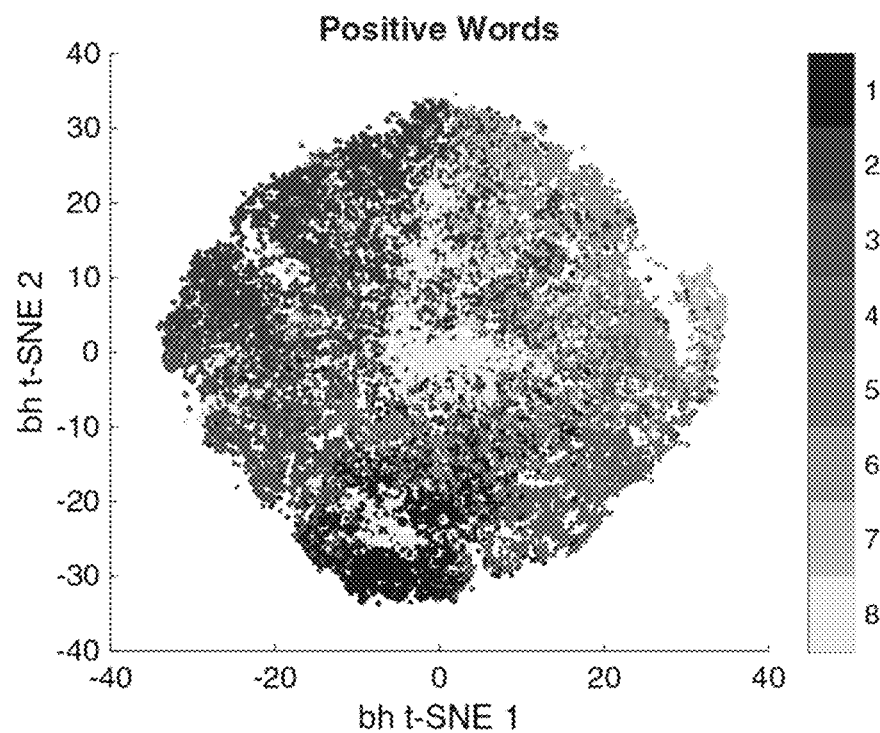
FIG. 12A illustrates the two dimensional visualization of the 64-dimensional descriptors for positive SoL words using the bh-tSNE algorithm.
Figure 12B:
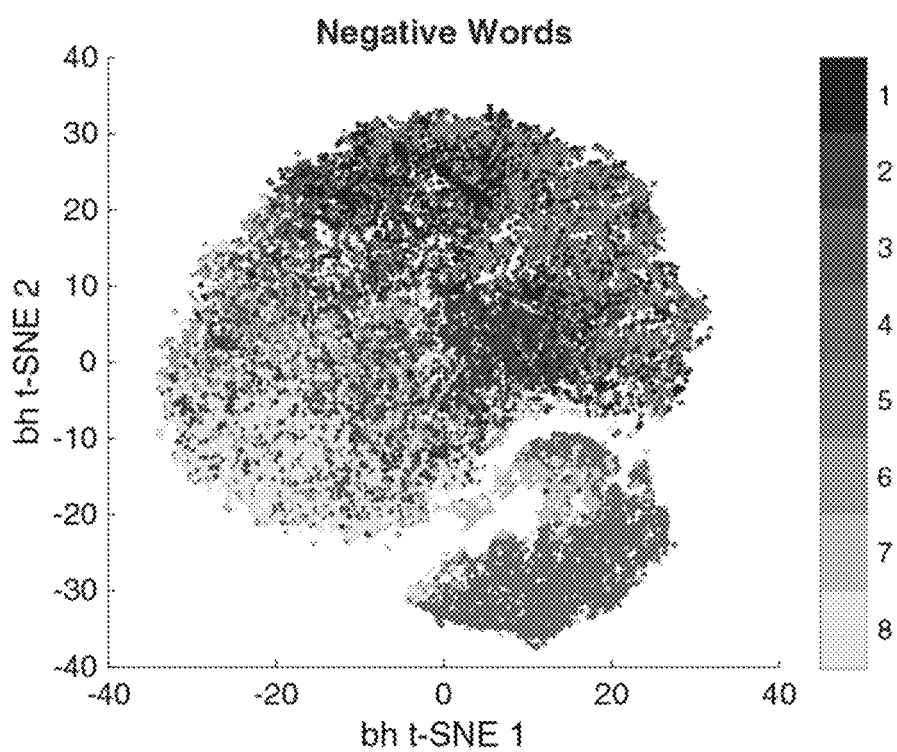
FIG. 12B illustrates the two dimensional visualization of the 64-dimensional descriptors for negative SoL words using the bh-tSNE algorithm.

In images of droplets 12, multiple levels of clustering are used. First, the SURF keypoints are separately clustered based on the SoL. This difference manifests itself when visualizing the keypoints via Barnes-Hut t-SNE dimensionality reduction. See Maaten et al., Accelerating T-SNE Using Tree-Based Algorithms. J. Mach. Learn. Res. 2014, 15, 3221-3245, which is incorporated by reference. In one embodiment, different clustering techniques are used for positive (+) SoL words and negative (−) SoL words. For example, positive SoL words are clustered via k-means clustering while negative SoL words are clustered using a gaussian mixture model. Gaussian mixture models are probabilistic models that assume all the data points are generated from a mixture of a finite number of Gaussian distributions with unknown parameters. Finally, keypoints are separated that have sharp and poor focus, based on their SURF metric. This allows one to separate keypoints derived from in-focus precipitate, out-of-focus precipitate, and non-specific image artifacts in the images. This creates four sub-categories of words: Strong-Negative, Weak-Negative, Strong-Positive, and Weak-Positive. FIG. 5 illustrates examples of visual words from each sub-category. Clusters are discovered using weak, low SURF metric keypoints, and are transferred to similar, stronger SURF keypoints that occupy the same 64-dimensional space using k-nearest neighbors. Corresponding weak and strong words (for a given sign of Laplacian) occupy the same 64-dimensional space, allowing them to be combined if separating by word strength does not provide utility. FIGS. 12A and 12B illustrate the two dimensional visualization of the 64-dimensional descriptors for positive words (FIG. 12A) and negative words (FIG. 12B) using the bh-tSNE algorithm. Keypoints with a positive SoL (FIG. 12A) are clustered into eight (8) visual words, and visualized with bh-tSNE representation created from positive keypoints only. Strong and weak sub-categories occupy the same region in 64-dimensional space, and are shown with the same labels and shading. Keypoints with a negative SoL (FIG. 12B) are also clustered into eight (8) visual words, and visualized with separate bh-tSNE representation. It is clear that negative words 4 and 7 have some distinctness from the rest of the keypoints.

Next, as seen in operation 350, a machine learning algorithm (e.g., Random Forest) is then trained by inputting the word frequency, total word count, and additional image features obtained from the droplets 12.

The dictionary size of the visual bag of words is determined by testing the precipitate classification performance with training and testing droplet sets. In the experiments conducted herein, all extracted droplets 12 were split into training, validation, and testing sets following 64:16:20 ratios, respectively. Then, random forest ensembles were created using the frequencies of visual words for all dictionary sizes as predictors for precipitate presence. While random forest was used for classification, any number of other classification schemes or methods such as Support Vector Machine (SVM), Adaptive Boosting (i.e., AdaBoost), Joint Boost, or Logistic Regression may also be used.

Precipitate is generally observed in the center of the droplet, so word clusters that are found in the center region of the image on average, are classified as likely precipitate words. Conversely, word clusters that are found outside the center region of the image, on average, are classified as likely non-precipitate words. Additional features are generated such as total number of words, total number of words in each sub-category (Positive-Weak, Negative-Strong, Positive-Strong, Negative-Weak), and count of likely-precipitate words. Finally, additional image features that quantify the contrast in the image by operating on a Laplacian of Gaussian transform of the image are added. Further image features that may be used for classification include the total number of strong/weak words in addition to all strong/weak words, excluding any strong/weak words that are likely non-precipitate words. Combinations of the above may also be used as features. For example, a combination of strongly negative words may be particularly helpful in clustering words.

Table 1 below illustrates additional image based features that may be used.

TABLE 1

| | |
|---|---|
| LOG_Min | Minimum value of Laplacian of Gaussian Transformation* of Image |
| LOG_Max | Maximum value of Laplacian of Gaussian Transformation of Image |
| LOG_STD_Min | Minimum value of normalized Laplacian of Gaussian Transformation of Image |
| LOG_STD_Max | Maximum value of normalized Laplacian of Gaussian Transformation of Image |
| DNAmask2_Record | Sum of thresholded absolute, normalized Laplacian of Gaussian Transformation of Image greater than 5 |
| DNAmask2_Record_4 | Sum of thresholded absolute, normalized Laplacian of Gaussian Transformation of Image greater than 4 |
| DNAmask2_Record_8 | Sum of thresholded absolute, normalized Laplacian of Gaussian Transformation of Image greater than 8 |
| LOG_Percentile_1 | 1st percentile of Laplacian of Gaussian Transformation of Image |
| LOG_Percentile_5 | 5th percentile of Laplacian of Gaussian Transformation of Image |
| LOG_Percentile_10 | 10th percentile of Laplacian of Gaussian Transformation of Image |
| LOG_Percentile_20 | 20th percentile of Laplacian of Gaussian Transformation of Image |
| LOG_Percentile_30 | 30th percentile of Laplacian of Gaussian Transformation of Image |
| LOG_Percentile_70 | 70th percentile of Laplacian of Gaussian Transformation of Image |

TABLE 1-continued

| | |
|---|---|
| LOG_Percentile_80 | 80th percentile of Laplacian of Gaussian Transformation of Image |
| LOG_Percentile_90 | 90th percentile of Laplacian of Gaussian Transformation of Image |
| LOG_Percentile_95 | 95th percentile of Laplacian of Gaussian Transformation of Image |
| LOG_Percentile_99 | 99th percentile of Laplacian of Gaussian Transformation of Image |
| LOG_STD | Standard deviation of Laplacian of Gaussian Transformation of Image |
| Img_STD | Standard deviation of Image |

*Normalized Laplacian of Gaussian Transformation has mean of 0, and standard deviation of 1.

Classification performance of dictionaries with sub-categories containing 1 to 8 words, different cutoffs to determine Strong/Weak words, and the addition of the image-based contrast-quantification features was compared. A model with eight (8) words in each sub-category (32 words overall), which incorporates image-based contrast-quantification features achieves the highest performance on the validation set, with specificity of 99.78%, and sensitivity of 97.86%. FIG. 5 illustrates exemplary images of different visual word clusters.

Figure 6A:
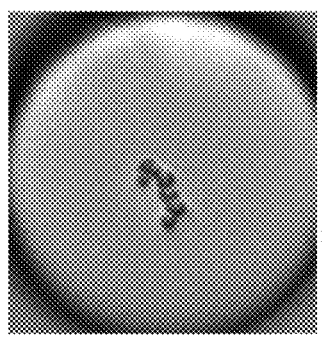
FIG. 6A illustrates sample droplets with precipitate.
Figure 6C:
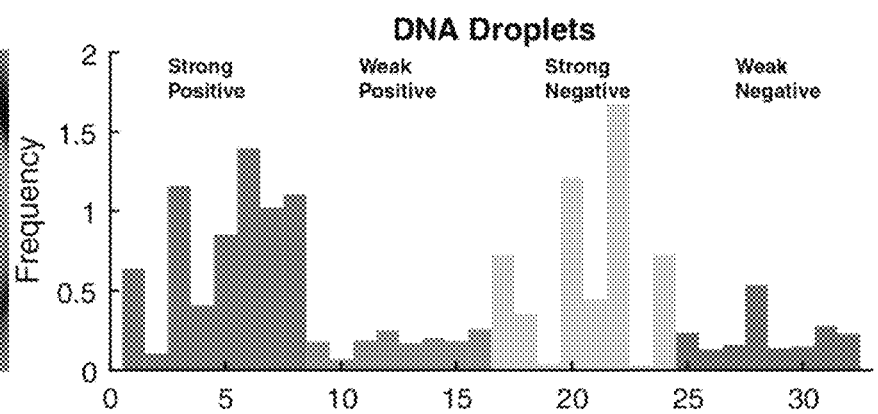
FIG. 6C illustrates average visual word frequencies for all droplets with precipitate.
Figure 6B:
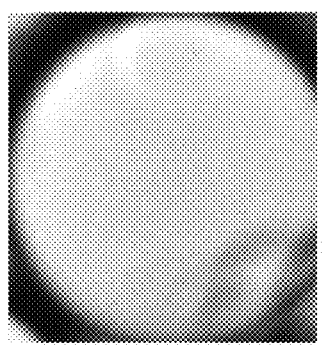
FIG. 6B illustrates sample droplets without precipitate.
Figure 6D:
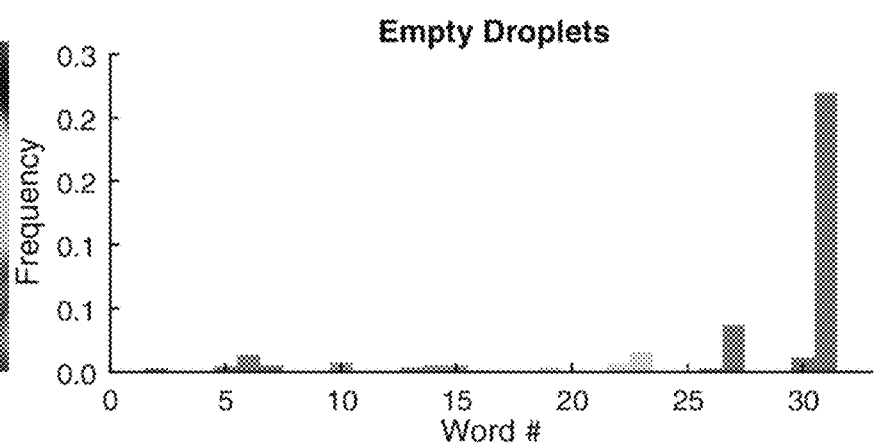
FIG. 6D illustrates average visual word frequencies for all droplets without precipitate.
Figure 7:
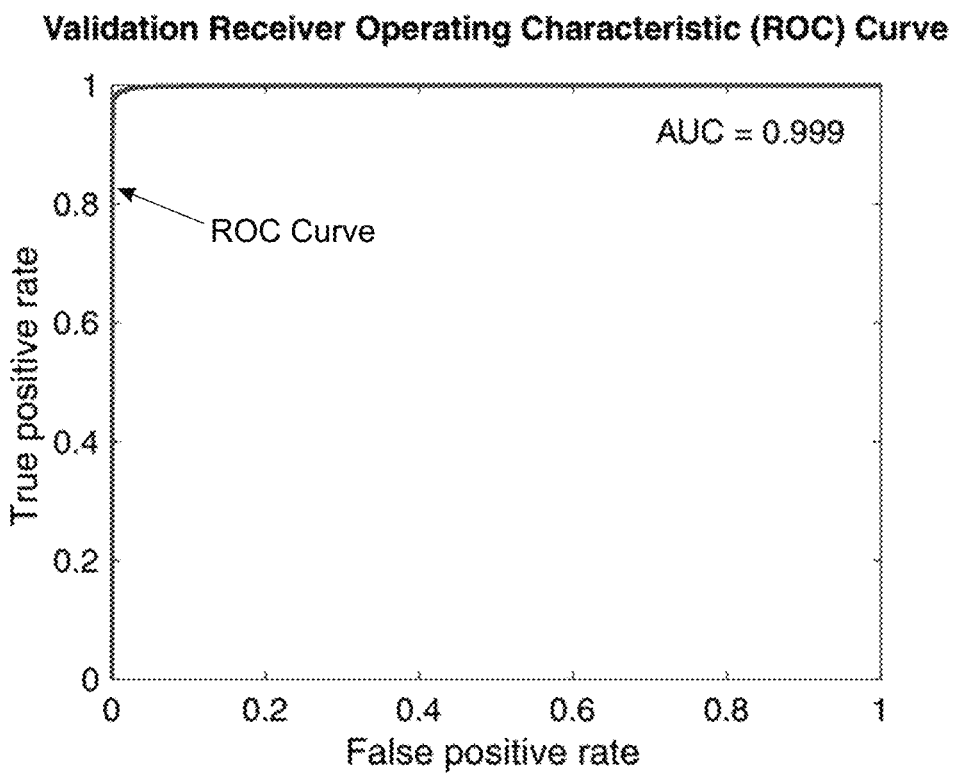
FIG. 7 illustrates the Receiver Operating Characteristic (ROC) for classification by using the random forest method.
Figure 8A:
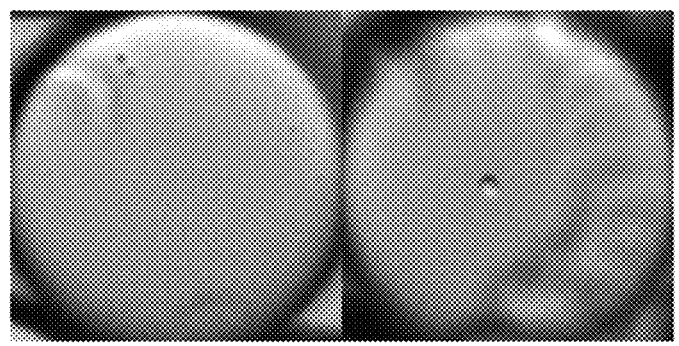
FIG. 8A illustrates examples of false positive droplets.
Figure 8B:
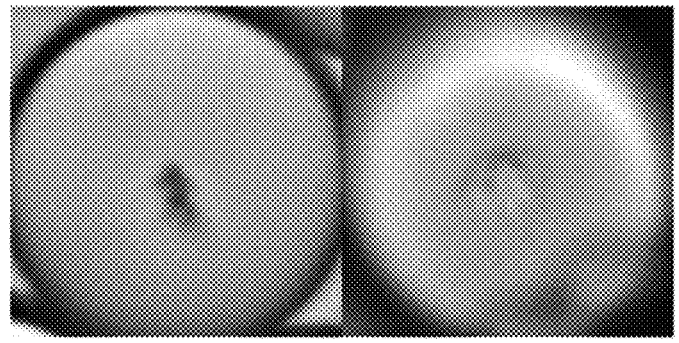
FIG. 8B illustrates examples of false negative droplets.

FIGS. 6A and 6B illustrate sample droplets 12 with and without precipitate with their respective average frequencies for all droplets with and without precipitate (FIGS. 6B and 6C). This model has Area Under the Curve (AUC) of the Receiver Operating Characteristic (ROC) of 0.999 for training and validation droplets 12 as seen in FIG. 7. This indicates how the model can be tuned in order to increase the true positive rate at the expense of the false positive rate. Examples of the droplets 12 falsely classified as containing droplets include those that contain oil droplets, or small particles picked up by the algorithm. FIGS. 8A and 8B illustrate examples of false positive (FIG. 8A) and false negative droplets (FIG. 8B). Positive droplets incorrectly classified often have out-of-focus precipitate, which generate few keypoints.

Figure 9:
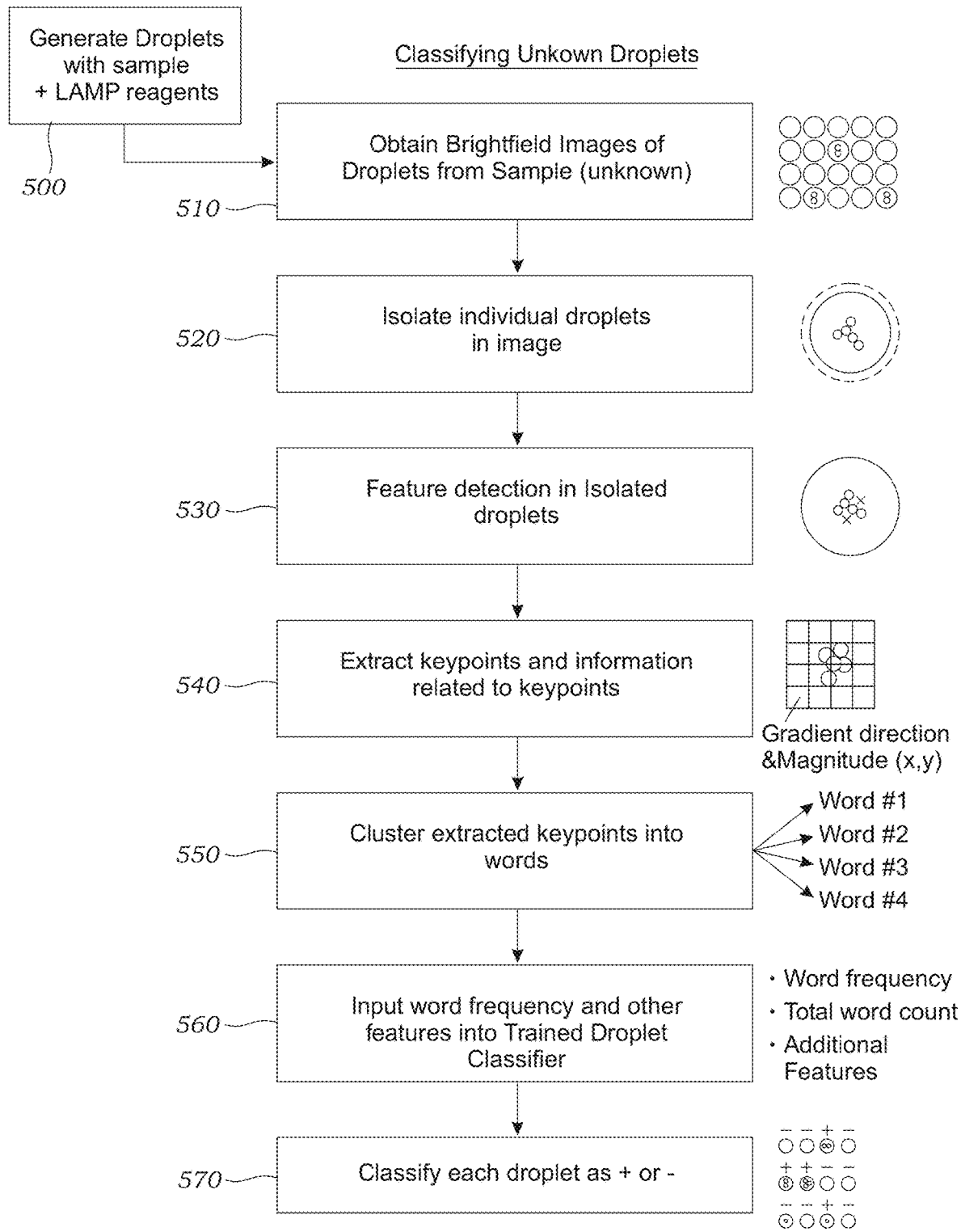
FIG. 9 illustrates a method or workflow that is used to classify unknown droplets as either positive (+) or negative (−).

FIG. 9 illustrates a method or workflow that is used to classify unknown droplets 12 as either positive (+) or negative (−). This, of course, assumes that the trained machine learning droplet classifier 66 has been trained as described above. As seen in FIG. 9, droplets 12 are generated in operation 500 that contain the nucleic target to be amplified along with the LAMP reaction mixture and DNA primers. The droplets 12 are then imaged in operation 510 using a brightfield imaging device 40. The image frame(s) 50 which contain the images of the droplets 12 are then transferred (if necessary) to the computing device 60 for image processing. In operation 520, individual droplets 12 are isolated using, for example, the circular Hough transform function imfindcircles in MATLAB (of course, other software programs may be used such as Python, C++, etc.). Image features are then detected in droplets 12 (operation 530) and keypoints and information related thereto are extracted as seen operation 540 as described previously. The extracted keypoints undergo additional clustering as seen in operation 550. The word frequency, total word count, and additional image features are then input into the trained machine learning droplet classifier 66 as seen in operation 560. Finally, each droplet 12 is classified as positive (+) or negative (−) as seen in operation 570. The image processing software 64 may then output the concentration of the target nucleic acid in the sample or a qualitative assessment of the sample as explained in operations 260, 270 of FIG. 2.

While embodiments of the present invention have been shown and described, various modifications may be made without departing from the scope of the present invention. For example, the method may applicable to other reactions that form precipitates and is not limited only to LAMP-based reactions. The invention, therefore, should not be limited, except to the following claims, and their equivalents.

What is claimed is:

1. An optical readout method for target nucleic acid detection comprising:
    generating a plurality of droplets containing a loop-mediated isothermal amplification (LAMP) reaction mix, DNA primers specific to a target nucleic acid, and the target nucleic acid sample;
    incubating the generated droplets;
    imaging the incubated droplets using a brightfield imaging device to obtain one or more images;
    subjecting the one or more images to image processing using image processing software executed on a computing device, wherein image processing comprises:
        isolating individual droplets in the one or more images;
        performing feature detection within the isolated droplets in the one or more images;
        extracting keypoints and information related thereto from the detected features within the isolated droplets;
        subjecting the extracted keypoints to a clustering operation to generate a plurality of words; and
        inputting the word frequency into a trained machine learning droplet classifier, wherein the trained machine learning droplet classifier classifies each droplet as positive or negative.

2. The method of claim 1, further comprising inputting total word count into the trained machine learning droplet classifier.

3. The method of claim 1, further comprising inputting additional image features into the trained machine learning droplet classifier.

4. The method of claim 3, wherein the additional image features comprise a compilation of strongly negative words.

5. The method of claim 3, wherein the additional image features comprise a compilation of strongly positive words.

6. The method of claim 1, wherein words are located in the center of the droplet are classified as likely precipitate words and words are located outside the center of the droplet are classified as likely non-precipitate words.

7. The method of claim 1, wherein the additional image features comprise statistical information of the Laplacian of Gaussian Transformation of the one or more images.

8. The method of claim 1, wherein the image processing software further outputs a concentration of the target nucleic acid based on the percentage or ratio of droplets that are classified as positive.

9. The method of claim 1, wherein the keypoints are extracted using Speeded Up Robust Features (SURF) or Scale Invariant Feature Transform (SIFT).

10. The method of claim 1, wherein the clustering comprises k-means clustering.

11. The method of claim 1, wherein the trained machine learning droplet classifier classifies each droplet using one of Support Vector Machine (SVM), Random Forest, Adaptive Boosting, Joint Boost, or Logistic Regression.

12. An optical readout method for detecting a precipitate contained within a droplet comprising:
   generating a plurality of droplets, at least some of the plurality of droplets comprising a precipitate generated during nucleic acid amplification contained therein;
   imaging the droplets using a brightfield imaging device to obtain one or more images;
   subjecting the one or more images to image processing using image processing software executed on a computing device, wherein image processing comprises:
      isolating individual droplets in the one or more images;
      performing feature detection within the isolated droplets in the one or more images;
      extracting keypoints and information related thereto from the detected features within the isolated droplets;
      subjecting the extracted keypoints to a clustering operation to generate a plurality of words; and
      inputting the word frequency into a trained machine learning droplet classifier, wherein the trained machine learning droplet classifier classifies each droplet as positive for the precipitate or negative for the precipitate.

13. The method of claim 12, further comprising inputting total word count into the trained machine learning droplet classifier.

14. The method of claim 12, further comprising inputting additional image features into the trained machine learning droplet classifier.

15. The method of claim 14, wherein the additional image features comprise a compilation of strongly negative words.

16. The method of claim 14, wherein the additional image features comprise a compilation of strongly positive words.

17. The method of claim 12, wherein words are located in the center of the droplet are classified as likely precipitate words and words located outside the center of the droplet are classified as likely non-precipitate words.

18. The method of claim 12, wherein the additional image features comprise statistical information of the Laplacian of Gaussian Transformation of the one or more images.

19. A system for the optical readout of droplets containing a precipitate therein comprising:
   a microfluidic device configured to generate a plurality of droplets, at some of the plurality of droplets comprising a precipitate generated during nucleic acid amplification contained therein;
   a brightfield imaging device configured to obtain an image of a field of view (FOV) containing the plurality of droplets;
   a computing device configured to execute image processing software, wherein image processing software is configured to:
      isolate individual droplets in the image;
      perform feature detection within the individual droplets in the image;
      extract keypoints and information related thereto from the detected features within the individual droplet;
      clustering the keypoints to generate a plurality of words; and
      input the word frequency into a trained machine learning droplet classifier executed by the image processing software, wherein the trained machine learning droplet classifier classifies each droplet as positive for the precipitate or negative for the precipitate.

* * * * *